United States Patent [19]
Montagnon et al.

[11] Patent Number: 4,525,349
[45] Date of Patent: Jun. 25, 1985

[54] PROCESS FOR THE LARGE-SCALE PRODUCTION OF A VACCINE AGAINST POLIOMYELITIS AND THE RESULTING VACCINE

[75] Inventors: Bernard J. Montagnon; Bernard J. C. Fanget, both of L'Arbresle, France

[73] Assignee: Societe Anonyme dite: Institut Merueux, Lyons, France

[21] Appl. No.: 335,352

[22] Filed: Dec. 29, 1981

[51] Int. Cl.³ .............................................. A61K 39/13
[52] U.S. Cl. ...................................................... 424/89
[58] Field of Search .................. 424/89; 435/237, 286, 435/241, 948

[56] References Cited

PUBLICATIONS

Van Wezel et al., Developments in Biological Standardization, vol. 42: 65–69, (1979), Large-Scale Concentration and Purification of Virus Suspension from Microcarrier Culture for the Preparation of Inactivated Virus Vaccines, (248 liters).

Thilly et al., Microcarrier Culture: A Homogeneous Environment for Studies of Cellular Biochemistry, (1979), in Jakoby (ed.), Methods in Enzymology Cell Culture, vol. 58, pp. 184–194, Large-Scale Scale-Up Accomplished Easily: (1000 ml. volume bottles for Microcarrier work).

Meignier, Developments in Biological Standardization, 42: 141–145, (1979), Cell Culture on Beads Used for the Industrial Production of Foot-and-Mouth Disease Virus, (150 liter Roux flask).

Giard et al., Biotechnology and Bioengineering, 21: 433–442, (1979), Human Interferon Production with Diploid Fibroblast Cells Grown on Microcarriers, (3× greater yield than roller bottles).

Van Wezel et al., Developments in Biological Standardization, 41: 159–168, (1978), New Approach to the Production of Concentrated and Purified Inactivated Polio and Rabies Tissue Culture Vaccines, (125 liters), (250 liters), (260 liters).

Van Wezel et al., Process Biochemistry, 13: 6–8, (1978), "Large Scale Cultivation of Animal Cells in Micro Carrier Culture", (200 liters).

Van Wezel et al., Devel. Biol. Stand., 40: 69–75, (1977), Production of an Inactivated Rabies Vaccine in Primary Dog Kidney Cells, (250 liters).

Levine et al., Somatic Cell Genetics 3: 149–155, (1977), Microcarrier Cell Culture: New Methods for Research-Scale Application, (large-scale concns attained).

Giard et al., Appl. & Envir. Microbiol., 34: 668–672, (1977), Virus Production with a Newly Developed Microcarrier System, (great promise for large-scale prod'n), (100 liter scale-up).

Spier et al., Biotechnology and Bioengineering, 18: 659–667, (1976), The Production of FMD Virus from BHK21C13 Cells Grown on the Surface of Deae Sephadex A50 Beads, (1000 liter scale-up).

Van Wezel, Nature, 216: 64–65, (1967), Growth of Cell Strains and Primary Cells on Micro-Carriers in Homogeneous Culture.

A. L. Van Wezel, Develop. Biol. Standard, vol. 47, pp. 7–13, (1981).

B. Mered et al., Develop. Biol. Standard, vol. 47, pp. 41–53, (1981).

B. J. Montagnon et al., Develop. Biol. Standard, vol. 47, I, pp. 55–64, II, pp. 151–155, (1981).

Eagle, Science, vol. 130, pp. 432–433, (1959).

WHO Expert Committee on Biological Standardization, 32nd Report, Technical Report Series No. 673, WHO-Geneva, (1982).

*Primary Examiner*—Shep K. Rose
*Attorney, Agent, or Firm*—Cushman, Darby and Cushman

[57] ABSTRACT

A process for large-scale production of poliomyelitis vaccine separately entails, for each type of poliomyelitis virus used, the following steps. A cell strain, using a cell stock, is multiplied by culturing the same in a liquid nutritive medium on microcarriers in suspension and by successive passages into biogenerator of increasing volumes. The last biogenerator is one having a capacity of at least 150 liters and the nutritive medium contains serum. This operation is carried out with stirring at a rate not greater than 40 rpm. At the end of the final passage the liquid nutritive medium is withdrawn and replaced by one that is serum-free. The biogenerator used for the last passage is then inoculated with virus which is permitted to develop, again with stirring at a rate not greater than 40 rpm. After virus culture, the liquid suspension is withdrawn, filtered, concentrated at least 150 times by ultrafiltration, subjected first to gel filtration and then to ion exchange chromatography. The resulting concentrated suspension is diluted with a serum-free medium and then inactivated. The suspensions of the respective types used are mixed from which individual dosages are prepared.

9 Claims, No Drawings

PROCESS FOR THE LARGE-SCALE PRODUCTION OF A VACCINE AGAINST POLIOMYELITIS AND THE RESULTING VACCINE

This invention concerns a new and useful process for the large-scale production of poliomyelitis vaccine as well as the poliomyelitis vaccine produced by said procedure.

Since 1954, the successive developement of the SALK vaccine (inactivated vaccine) and the SABIN vaccine (live vaccine) and the massive vaccination programs carried out using them have made it possible effectively to control the disease of poliomyelitis in the industrial countries. However, the incidence of the disease is still high in warmer countries where, for unexplained reasons, the live vaccine is ineffective and the inactivated vaccine seems poorly adapted to large scale vaccination programs because of financial and logistical considerations, such as the need to administer multiple doses.

Even in the industrial countries, where the live vaccine is used on a massive scale, the disease has not completely disappeared, and about half the residual cases are brought on by the administration of the vaccine, occurring either in the vaccinated party himself or, by contact, in his family or close associates.

There is hence a need for a new vaccine which overcomes these drawbacks.

More specifically, it would be desirable to have an inactivated vaccine so as to avoid reinseminating the environment with a weakened poliomyelitis virus which might, by mutation, regain its virulence. Such an inactivated vaccine should have a high level of effectiveness so as to achieve a seroconversion rate verging on one hundred percent after only two injections. Preferably, the vaccine should be able to be associated with other standard vaccines, and it must be possible to use it in small volumes so that it can be administered rapidly and on a large scale, especially be using a needleless injector. Finally, this vaccine should have a particularly low cost price so that it can be used on a massive scale even in the nonindustrial countries.

One of the principal components of the cost price of a viral vaccine such as a poliomyelitis vaccine is the cell culturing required for the multiplication of the virus. As it happens, extremely significant progress has been made in this area, on the one hand by the development of cell strains which can easily be reproduced on a large scale, and on the other hand by microcarriers for the cells making it possible to work with cell cultures in suspension in nutritive media in substantial volumes (see, for example, A. L. Van Wezel, "New Trends in the Preparation of Cell Substrates for the Production of Virus Vaccines," *Progr. Immunobiol. Standard*, Vol. 5 (Karger: Basel, 1972), pp. 187-192; and "Tissue Culture Technology in Virus Vaccine Production," Symposium on Tissue Culture Technology at the 75th National Meeting of the American Institute of Chemical Engineers, Detroit, Michigan, U.S.A., June 3-6, 1973). Poliomyelitis vaccine production processes using cell cultures in suspension have also been proposed by Van Wezel et al. in "New Approach to the Production of Concentrated and Purified Inactiv[at]ed Polio and Rabies Tissue Culture Vaccines," *Develop. Biol. Standard*, Vol. 41 (S. Karger: Basel, 1978), pp. 159-168; 15th IABS Congress, "Vaccinations in the Developing Countries: La Guadeloupe 1978," in Large-Scale Concentration and Purification of Virus Suspension from Microcarrier Culture for the Preparation of Inactivated Virus Vaccines," *Develop. Biol. Standard*, Vol. 42 (S. Karger: Basel, 1979), pp. 65-69; 2nd General Meeting of ESCAT, Paris, 1978; and in "The Production of Inactivated Polio Vaccine on Serially Cultivated Kidney Cells from Captive-Bred Monkeys," *Develop. Biol. Standard*, Vol. 46 (S. Karger: Basel, 1980), pp. 151-158; 3rd General Meeting of ESCAT, Oxford 1979.

Finally, in a quite recent publication, Van Wezel referred to the use of a strain of cells from the kidneys of the African green monkey, described by Yasamura Y. in "Establishment of a Cell Strain Derived from Monkey Kidney (*C. Aethiops*)," 14th Meeting of the Japanese Tissue Culture Association, October 1962 in Tokyo, and available from the American Type Culture Collection under No. ATCC-CCL 81 (124th passage).

For the time being, however, these proposals have not made it possible to find a vaccine which might actually be produced in industrial quantities while meeting the demands formulated above. Among the other problems not yet satisfactorily resolved is the difficulty of obtaining sufficiently stable type 1 antigens, Mahoney type for example, in such a poliomyelitis vaccine.

It is hence one objective of this invention to provide a process for the large-scale production of poliomyelitis vaccine which is easy to implement and has a very low cost price.

Another objective of the invention is to provide such a process which makes it possible to have a stable vaccine which includes type 1, 2 and 3 antigens in effective proportions.

A further objective of the invention is to provide such a process which makes it possible to obtain a vaccine characterized by a high antigenic value in a small volume.

The process according to the invention entails separately, for each type of poliomyelitic virus, the stages consisting in multiplying a cell strain, preferably the VERO strain, from a cell stock by culturing on microcarriers in suspension by means of successive passages into increasing volumes of biogenerators, the last passage being carried out in a biogenerator whose tank holds at least 150 liters, into a suitable nutritive medium, drawing off the liquid medium at the end of the final passage and replacing it by a new liquid medium containing no serum, inoculating the biogenerator of the last virus passage, preferably maintaining the temperature in the vicinity of 35° C. to 37° C., the pH in the vicinity of 7.4 to 7.8 and the partial oxygen pressure in the vicinity of 10 percent, withdrawing the liquid suspension after virus culture, filtering the suspension drawn off, concentrating the filtered suspension at least 150 times, and preferable five hundred times, by means of ultrafiltration, carrying out a gel filtration of the concentrated suspension, subjecting the suspension obtained to an ion exchange chromatography, diluting the concentrated suspension obtained with a serum-free medium to obtain a dilution of the order of 7 to 8 times, so as preferably to be concentrated 50 times with respect to the initial viral harvest, inactivating the suspension thus diluted and purified, preferably by means of the action of formol and heat at 37° C., preferably after a filtration, and then mixing the three suspensions of the respective types 1, 2 and 3, and preparing the individual doses.

Preferably, starting from the VERO cell stock, cells are harvested by digestion with a solution of typsin buffered with sodium citrate, followed by a passage into a 20 liter biogenerator, then a new passage into a 150 liter biogenerator, then a final passage using an extremely high volume biogenerator, 1,000 liters for example, or several 150 liter biogenerator, with the inoculation by the virus being carried out in the course of this last passage after washing by the new serum-free medium.

Passage from one biogenerator to the other uses a trypsination in situ in the vat itself from the one liter biogenerator to the 1,000 liter one. Preference is given to the use of a highly diluted solution of purified trypsin, between 0.005 percent and 0.05 percent, preferably 0.025 percent. The balls with the cells are recovered in a sterile receptacle with a vibrating stirrer, with the mixture kept continuously in moderate vibration to detach the cells thoroughly without damaging them. The mixture is harvested in calf serum to inactivate the trypsin, then inoculated in a suspension of new balls in the following biogenerator in a reduced volume, for example 1/10 that of the culture passage proper.

The microcarriers used are preferably spherical balls with an average diameter of about 50 to 300μ in the dry state and a density slightly greater than 1, made up of dextran polymers and bearing on their surface grafted radicals of DEAE (di-ethyl-aminoethyl). Preferably, the concentration of microcarrier in terms of weight is between 1 and 5 grams of microcarrier per liter of medium, preferably 1.5.

The temperature of the culture is maintained between 35° C. and 38° C.

Preferably, each passage lasts six to eight days with stirring; customarily, upon conclusion of culturing, there will be a cell growth representing a multiplication of eight to twenty times.

Stirring is a critical point of the process in the vats of large biogenerators. Preferably, this stirring is effected at a rate of 10 to 40 rotations per minute, for example with a stirrer rotating about a vertical axis and featuring triangular blades of which one side is provided with a vane which makes a rather small angle with the plane of the blade.

The culture medium for the cell passages is preferably a customary medium such as Eagle's "Minimum Essential Medium, " enriched with lactalbumin hydrolysate, glucose and calf serum. The washing and growth medium for the virus is preferably medium 199 from Parker.

Preferably, the inoculation of the last cell passage with virus is effected at a quantity ratio of 0.1 to 0.5 $TCID_{50}$ of virus per cell.

In one particularly preferred mode of use, in which VERO cell strains are utilized, a cell stock situated in a cell bank at the 137th passage is used. The growth of the cells is then brought about by the successive passages referred to above so as to obtain the 142nd passage, in the course of which the virus inoculation is carried out.

The inactivation is preferably effected on the concentrated and purified viral suspension heated to a temperature of 37° C. and preferably filtered for twenty-four hours before the inactivation is started at a temperature of 37° C. A formol solution is then added to achieve a concentration of 1 per 4,000. Stirring is continued for at least 4 days, preferably with one or several intermediary filtrations in the course of inactivation, which preferably lasts twelve days in all.

The inactivated vaccine obtained by the process according to the invention includes the three strains of poliomyelitic viruses, preferably Mahoney for type 1, MEF 1 for type 2, and Saukett for type 3. This vaccine, monitored to verify the absence of living virus on cell cultures, preferably has, in vaccinating doses expressed as the contents of the specific poliomyelitic vaccinating antigen, known as "antigen D," a composition with the following proportions: 40 units of antigens D for type 1, 8 units of antigens D for type 2, and 32 units of antigens D for type 3.

By way of example, an individual dosage in a volume of 0.5 ml of vaccine according to the invention includes 40 D units for type 1, 8 D units for type 2, and 32 D units for type 3. It also contains 10 micrograms of phenol red, 2.5 microliters of 2-phenoxyethanol, 2.5 microliters of ethanol and 12.5 micrograms of formol.

The antibiotics used in the manufacturing process are no longer measurable in the finished product because of the intervening purification.

The invention will now be described by way of non-restrictive example.

CELL MULTIPLICATION

The VERO strain as distributed by the American Type Culture Collection under No. ATCC-CCL 81 is used. This cell is at its 124th passage. A working cell stock obtained during the 137th passage is prepared in a conventional manner. The stock is distributed into phials preserved in liquid nitrogen. Each phial contains about $100 \times 10^6$ cells.

For preparation of the working cell stock, a phial of cells (ATCC-CCL 81 - VERO F 1415) is taken at the 124th passage and a series of subcultures are made in Roux dishes until the 135th passage inclusive, gradually increasing the total surface area of the dishes. The 136th and 137th passages are carried out in 20 liter and 150 liter biogenerators. The harvest obtained is placed in phials of $100 \times 10^6$ cells which are frozen and used in industrial production, which is described below. It is possible to obtain 300 phials at the 137th passage from the initial phial at the 124th passage.

The liquid medium used for the successive passages, including for the establishment of the cell stock, is Eagle's "Minimum Essential Medium" in an Earle saline solution enriched with 0.2 percent lactalbumin hydrolysate, 0.1 percent glucose or fructose, and 5 percent calf serum. Each milliliter of medium contains 75 units of streptomycin, 14 units of neomycin, and 35 units of polymyxin B sulfate.

The microcarrier balls used are DEAE dextran balls sold under the trade name CYTODEX by the Swedish company Pharmacia. In the dry state these balls have an average diameter of about 67 micrometers and a density of 1.03. One gram of dry balls contains approximately $5 \times 10^6$ balls, corresponding to a total surface area per gram of about 0.6 m². The concentration of balls per liter of medium is of the order of 1.5 g/l.

In order to prepare the balls, they are first allowed to swell in a buffer solution, washed, and then sterilized, for example in a vat of at least 150 liters, with stirring.

To bring about the multiplication, the contents of one phial at the 137th passage are poured into a biogenerator containing one liter of medium with the balls at the above-mentioned density. The culture is kept at a temperature of 37° C. for 6 or 7 days with stirring at the rate of twenty rotations per minute, with the stirring gradually being increased. At the end of the growth, i.e., after the 6th or 7th day, the liquid medium is evacuated and the cells fixed on the balls are retained. The cells are detached with the help of a 0.025 percent solution of crystallized trypsin buffered with sodium citrate 0.125 M. The cells, which have thus just completed their 138th passage, are then brought to a 5 liter biogenerator where, in the same manner and under the same conditions, the 139th passage occurs. A 140th passage is then carried out in a biogenerator containing 20 liters of medium, then the 141st passage is carried out in a 150 liter biogenerator. The 142nd passage is then effected in a one thousand liter vat containing 1,000 liters of medium. The volumes indicated are usable volumes.

Stirring in the vats is effected by means of a beater consisting of a rotary vertical axis plunged into the liquid suspension and featuring, at its lower end, two or more blades each of which has the general shape of a right triangle, where one of the sides of the right angle, preferably the larger one, is soldered along a vertical generating line of the axis, with the right angle itself more or less at the lower end of the axis. The blades are thus arranged in one or several vertical radial planes, with the second side of the right angle, largely horizontal, arranged radially at the lower end. Every second side is extended downward by a rather short rectangular vane making an angle of 10° to 45° with the plane of the blade, said vane having a rectangular shape with one of the long sides being in common with the said second side of the right angle. The surface area of the vane is between ½ and 1/10 that of the trangular blade.

MULTIPLICATION OF THE VIRUS

The three following strains of poliomyelitic virus are used separately: Mahoney for type 1; MEF 1 for type 2; Saukett for type 3. These strains are well known in the literature and are available, for example, at the Rijksinstituut voor de Volksegezondheid, Bilthoven, Netherlands.

Before undertaking the seeding proper, the stirring is stopped after the seventh or eighth day of growth at the 142nd passage of cells. The balls settle to the bottom of the vat and the liquid culture medium is drawn off. A Parker 199 medium is then added in an Earle saline solution enriched with 0.1 percent glucose, serum-free, and there is stirring for one half hour. This makes it possible to wash the cells. This medium is then drawn off in turn.

The vat is refilled with the same Parker 199 medium containing the same antibiotics as the above-mentioned Eagle medium.

The next step is the inoculation of the virus. For example, if 150 liter biogenerators are used instead of a 1,000 liter vat, 20 liters of serum-free 199 medium are first put into the vat containing the microcarriers and the cells, after which 500 milliliters of the viral seed lot are added to achieve a virus concentration of 0.3 $DICI_{50}$ per cell.

The virus is allowed to be adsorbed on the cells for a half hour while stirring gently at 30 rotations per minute, after which the volume is brought up to 150 liters with the Parker medium. The pH is adjusted to 7.4, stirring sped up to 40 rotations per minute, the temperature kept at 36° C. and the $pO_2$ to 10 percent. The virus culture then works for 72 hours.

At the end of the culture, stirring is stopped and harvesting is carried out by drawing off the culture medium constituting the viral suspension. The harvest is filterd on a 0.22 micron cellulose ester membrane and stored at +4° C.

CONCENTRATION AND PURIFICATION

The harvest filtered as above is then subjected to ultrafiltration on a cellulose ester ultrafiltering Millipore membrane whose molecular separation power is situated at a molecular weight of at least 10,000. The filtering liquid, i.e., the ultrafiltrate, is discarded and that which is retained by the membrate, i.e. the ratainate is retained.

The concentrated suspension obtained is then placed on a gel filtration column containing an agarose gel, for example sepharose CL6B, balanced at pH 7 with a 0.04 M phosphate buffer. The effluent is measured with an ultraviolet ray spectrophotometer at two wave lengths, 254 nanometers for the nucleic acids and 280 nanometers for the proteins. The corresponding volume of effluent is gathered at the virus output peak and we thus obtain, for one liter of concentrated viral suspension, 5 liters of viral suspension in a phosphate buffer.

This suspension is then put into an ion exchange chromatography column containing a DEAE dextran silica (Spherosil) network balanced at pH 7 with 0.04M phosphate buffer. The output volume collected measures about 4 liters for every 5 starting liters.

The first gel filtration made it possible to eliminate most of the proteins, lipoproteins and other impurities, with the larger viral particles being exluded first.

During chromatography, the proteins and other impurities are retained because of their affinity with the DEAE radicals, while the virus passes freely.

The concentrated and purified viral suspension emerging from the chromatography column is diluted with serum-free and antibiotic-free 199 medium to achieve a 50 to 1 dilution.

The product may be preserved at +4° C. pending the inactivation stage.

INACTIVATION

Before inactivation, the viral suspension is filtered on a 0.22 micron cellulose ester membrane.

It is heated to 37° C. with steady magnetic stirring for 24 hours. The formol solution is then added to achieve a concentration of 1 per 4,000. While keeping the viral suspension at 37° C., the magnetic stirring is continued for the first four days. On the sixth day, the viral suspension is filtered on a 0.22 micron cellulose ester membrane. Inactivation is then continued under suspension at 37° C. until the twelfth day. The inactivated viral suspension is homogenized and may be stored, at +4° C. for example.

PREPARATION OF THE CONCENTRATED TRIVALENT BATCH

Starting with the three inactivated monovalent suspensions, the necessary volume of each suspension is taken to obtain a final mixture of three types containing 400 D antigen units for type 1, 80 D anitgen units for type 2, and 320 D antigen units for type 3, and the mixture is completed with the addition of an amount of 199 medium sufficient for a pH of 7.2 and a total volume of one milliliter.

As an example, there are prepared an inactivated type 1 suspension having a concentration of 1600 D antigen units per ml, a type 2 suspension having 800 D antigen units per ml and a type 3 suspension having 1600 D antigen units per ml. There are then admixed 1250 ml of the type 1 suspension, 500 ml of the type 2 suspension and 1000 ml of the type 3 suspension. To the resulting admixture there are added 2250 ml of 199 medium so as to obtain an overall volume of 5000 ml.

The mixture is homogenized, cellulose ester membrane filtration is carried out, and we obtain a concentrated trivalent suspension whose concentration is sufficient to allow for the possiblility of associating it with one or several associated vaccines, such as antidiphtheria vaccine, antitetanus vaccine, or vaccines against whooping cough.

PREPARATION OF FINAL DOSAGES

Assuming it is desired to obtain a vaccine only against poliomyelitis without any associated vaccine, the above concentrated trivalent suspension is diluted with 199 medium at pH 7.2 so that the unit dosage of 0.5 milliliter contains 40 D antigen units for type 1, 8 D antigen units for type 2, and 32 D antigen units for type 3.

To do so, the necessary quantities of concentrated trivalent suspension are added in succession to a sterile receptacle, followed by sterile 199 medium, then by a solution of 2-phenoxyethanol in pure alcohol, then a titrated solution of formol at 35 percent, so as to obtain a final concentration of 0.5 percent of 2-phenoxyethanol and twenty-five micrograms per milliliter of formol.

This suspension is then distributed into 0.5 milliliter dosages in auto-injectable syringes.

It goes without saying that during the process, at the different stages of production, the usual activity and sterility checks are carried out. It will thus be possible to check the cells of the strain by sampling, with the cells being incubated and then tested, for example, for hemadsorption on guinea pig red corpuscles. Identity tests will also be carried out by characterization of the isoenzymes. It will also be possible to carry out mycoplasm research.

Determination of the viral strength is by measuring the cytopathogenic effect of successive dilutions of the virus. In addition, bacterial and fungous sterility tests will be carried out at various times. Inactivation will be checked by sampling at various times, comparing the inactivation curve with a standard curve established by experience.

We claim:

1. Process for the large-scale production of poliomyelitis vaccine separately entailing, for each type of poliomyelitis virus used, stages consisting in multiplying a VERO cell strain beginning with a cell stock by means of culturing on microcarriers in suspension in a liquid nutritive medium, said microcarriers being balls with an average diameter of about 50 to 300 microns in the dry state and with a density very slightly greater than 1, made of dextran polymers and bearing on their surfaces grafted radicals of di-ethyl-amino-ethyl, with the concentration of microcarriers in terms of weight being between 1 and 5 grams per liter of said liquid medium, by successive passages into increasing volumes of biogenerators, each passage being carried out for six to eight days, the last passage being carried out in a biogenerator whose tank holds at least 150 liters, said liquid nutritive medium containing serum, while stirring at a rate not greater than 40 r.p.m., drawing off the liquid nutritive medium at the end of the final passage and replacing it by another liquid medium containing no serum, inoculating the biogenerator of the last passage with virus, allowing the virus to develop at a temperatue between 35° C. and 37° C., a pH in the vicinity of 7.4 and a partial oxygen pressure in the vicinity of 10 percent, while stirring at a rate not greater than 40 r.p.m., withdrawing the liquid suspension after virus culture, filtering the suspension drawn off, concentrating the filtered suspension at least 150 times by means of ultrafiltration, carrying out a gel filtration of the concentrated suspension, subjecting the suspension obtained to ion exchange chromatography, diluting the concentrated suspension obtained with a serum free medium, inactivating the suspension thus diluted and purified, then mixing the suspensions of the respective types used and preparing the individual dosages.

2. Process according to claim 1, in which the 138th passage is carried out in a biogenerator of about 1 liter, the 139th passage in a biogenerator of about 5 liters, the 140th passage in a biogenerator of about 20 liters, the 141st passage in a biogenerator of about 150 liters, and the 142nd passage, with the viral multiplication, in a larger volume yet.

3. Process according to claim 1, in which a concentration of the order of five hundred times is achieved by ultrafiltration.

4. Process according to claim 1 in which the said concentration is 1.5.

5. Process according to claim 1, in which the inoculation is carried out at the ratio of a quantity of 0.1 to 0.5 $DICT_{50}$ of virus per cell.

6. Process according to claim 1, in which the cell culture is carried out in the presence of antibiotics.

7. Process according to claim 1, in which the culture medium is stirred with a slow stirrer with a rotary axis extending into the medium and equipped with triangular blades ending in vanes tilted with respect to the radial plane of the blade.

8. Process according to claim 7, in which the virus development is carried out in a 1,000 liter vat.

9. Process for the large-scale production of poliomyelitis vaccine separately entailing, for each type of poliomyelitis virus used, stages consisting in multiplying a VERO cell strain beginning with a cell stock by means of culturing on microcarriers in suspension in a liquid nutritive medium, said microcarriers being balls with an average diameter of about 50 to 300 microns in the dry state and with a density very slightly greater than 1, made of dextran polymers and bearing on their surfaces grafted radicals of di-ethyl-aminoethyl, with the concentration of microcarriers in terms of weight being between 1 and 5 grams per liter of said liquid medium, by successive passages into increasing volumes of biogenerators, each passage being carried out for six to eight days, the last passage being carried out in a biogenerator whose tank holds at least 150 liters, said liquid nutritive medium containing serum, while stirring at a rate not greater than 40 r.p.m., whereby at the end of each passage to be followed by a subsequent passage the cells are detached from the microcarrier balls using a solution of cyrstallized trypsin having a concentration between 0.005 percent and 0.05 percent, drawing off the liquid nutritive medium at the end of the final passage and replacing it by another liquid medium containing no serum, inoculating the biogenerator of the last passage with virus, allowing the virus to develop at a temperature between 35° C. and 37° C., a pH in the vicinity of 7.4 and a partial oxygen pressure in the vicinity of 10 percent, while stirring at a rate not greater than 40 r.p.m., withdrawing the liquid suspension after virus culture, filtering the suspension drawn off, concentrating the filtered suspension at least 150 times by means of ultrafiltration, carrying out a gel filtration of the concentrated suspension, subjecting the suspension obtained to ion exchange chromatography, diluting the concentrated suspension obtained with a serum free medium, inactivating the suspension thus diluted and purified, then mixing the suspensions of the respective types used and preparing the individual dosages.

* * * * *